United States Patent [19]

Oonishi et al.

[11] Patent Number: 5,149,640
[45] Date of Patent: Sep. 22, 1992

[54] METHOD FOR PRODUCING GALACTOSE TRANSFER PRODUCTS

[75] Inventors: Norimasa Oonishi; Kenzo Yokozeki, both of Kawasaki, Japan

[73] Assignee: Ajinomoto Co., Inc., Tokyo, Japan

[21] Appl. No.: 454,944

[22] Filed: Dec. 22, 1989

[30] Foreign Application Priority Data

Dec. 22, 1988 [JP] Japan ............................. 63-324855
Jun. 29, 1989 [JP] Japan ............................. 1-168103

[51] Int. Cl.$^5$ ..................... C12P 19/02; C12P 19/12; C12P 19/44; C12R 1/01
[52] U.S. Cl. ................................. 435/100; 435/71.1; 435/74; 435/87; 435/88; 435/89; 435/90; 435/101; 435/193; 435/822; 435/911
[58] Field of Search ............... 435/822, 911, 101, 100, 435/71.1, 74, 87, 88, 89, 90, 193

[56] References Cited

U.S. PATENT DOCUMENTS 4,435,389 3/1984 Mutai et al. ..................... 435/244
4,957,860 9/1990 Kan et al. ........................ 435/101

FOREIGN PATENT DOCUMENTS 58-20266 7/1983 Japan .

OTHER PUBLICATIONS

Derwent Abs 89-140776/19 Asahi Chem Ind KK (J01085090) Mar. 1989.
Biotechnology Letters, 9, 387 (1987).

Primary Examiner—Herbert J. Lilling
Attorney, Agent, or Firm—Oblon, Spivak, McClelland, Maier & Neustadt

[57] ABSTRACT

A galactose transfer product is prepared by a process of allowing a microorganism capable of producing a galactose transfer product of the formula: $(Gal)_n$—R, wherein Gal represents a galactose residue, n represents an integer of 1 to 4 and R represents a galactose receptor to act on a combination of lactose or a galactose donor and a galactose receptor; and collecting the galactose transfer product produced.

11 Claims, No Drawings

METHOD FOR PRODUCING GALACTOSE TRANSFER PRODUCTS

BACKGROUND OF THE INVENTION

1. Field of the Invention

The present invention relates to a method for producing a galactose transfer product.

2. Description of the Background

In recent years, attention has been directed to compounds which contain a galactose residue, especially transfer products of sugar (especially lactose), which can be used as a factor for the proliferation of Bifidobacteria (BIFIDUS, Vol. 2, No. 2, 1989). In addition, a change in physical properties such as increased solubility, or the like is noted in transfer products to sugar alcohols, nucleosides, alcohols, and the like. These transfer products are of high utilization value in their application to drugs, and the like.

A method which is known for producing galactose transfer products uses β-galactosidase of *E. coli*. In the method the galactose residue is transferred to fructose or N-acetylglucosamine (Biotechnology Letters, 9, 243 (1987)) or the galactose residue is transferred to nucleosides such as adenosine, or the like. (Journal of Agricultural Association, Japan, 48, 605 (1979)). However, these methods have the disadvantage that the yield of transfer products production is poor. Another method for producing galactose transfer product (galacto-oligosaccharide), wherein the galactose donor is lactose and the galactose receptor is lactose, is known in which the β-galactosidase of *Aspergillus oryzae* is used (Published Examined Japanese patent application no. 58-20266). However, the method is not very practical since the yield of galacto-oligosaccharide is poor. A need therefore continues to exist for an improved method of producing a galactose transfer product.

SUMMARY OF THE INVENTION

Accordingly, one object of the present invention is to provide a method of preparing a galactose transfer product in enhanced yields which is industrially acceptable.

Briefly, this object and other objects of the invention as hereinafter will become more readily apparent can be attained in a process of preparing a galactose transfer product by allowing a microorganism capable of producing a galactose transfer product of the formula: $(Gal)_n$—R, wherein Gal represents a galactose residue, n represents an integer of 1 to 4 and R represents a galactose receptor to act on a combination of lactose or a galactose donor and a galactose receptor; and collecting the galactose transfer product produced.

DETAILED DESCRIPTION OF THE PREFERRED EMBODIMENTS

In the investigation leading to the present invention a survey was made for microorganisms which are capable of producing and accumulating galactose transfer product from lactose or a galactose donor such as o-nitrophenyl-β-D-galactopyranoside, or the like, and a galactose receptor such as sugar, a sugar alcohol, nucleosides, alcohols or derivative thereof, in a high yield at a high rate of accumulation. As a result, it has been found that microorganism strains belonging to the genus Rhodotorula, the genus Sterigmatomyces, the genus Cryptococcus, the genus Geotrichum, the genus Apiotrichum, the genus Corynebacterium, the genus Bacillus, the genus Flavobacterium, the genus Rhizobium or the genus Sirobasidium can produce galactose transfer products from lactose or a galactose donor such as o-nitrophenyl-β-D-galactopyranoside, or the like and a galactose receptor such as sugar, a sugar alcohol, a nucleoside, an alcohol or derivatives thereof, at an extremely high rate of accumulation and yield.

Specific examples of the microorganisms include i Rhodotorula minuta IFO 879, *Sterigmatomyces elviae* AJ 14199 (FERM BP-2586,FERM P-10001), *Cryptococcus laurentii* IFO 609, *Geotrichum amycelicum* AJ 14196 (FERM P-10071), *Apiotrichum humicola* ATCC 14438, *Corynebacterium michiganense* ATCC 492, *Bacillus megaterium* AJ 1272 (FERM P-3747), *Flavobacterium aurantianum* AJ 2462 (FERM.P-10069), *Rhizobium meliloti* AJ 2823 (FERM P-8197) and *Sirobasidium magnum* CBS 6803.

For the culturing of these microorganisms, any nutrient source is usable as long as it can be assimilated by the microorganism. Appropriate culture media can be formulated with, for example, carbohydrates such as glucose, sucrose, and the like; alcohols such as ethanol, glycerol and the like; organic acids such as acetic acid, propionic acid, and the like; carbon sources such as soybean oil, and the like or a mixture thereof; nitrogen-containing inorganic or organic nutrient sources such as yeast extract, peptone, meat extract, corn steep liquor, ammonium sulfate, ammonia, and the like; inorganic nutrient sources such as phosphates, magnesium, iron, manganese, potassium, and the like; vitamins such as biotin, thiamine, and the like. For culturing, the pH of the nutrient medium should be within the range of from 4.0 to 9.5 and culturing is carried out aerobically at a temperature ranging from 20° to 40° C. for 12 hours to 5 days.

In order to produce the galactose transfer product, the culture medium is supplemented with lactose or galactose donors such as o-nitrophenyl-β-D-galactopyranoside, or the like and galactose receptors such as sugar, sugar alcohols, nucleosides, alcohols and derivatives thereof, or the like at the initial stage of culturing or during the culturing. Alternatively, the galactose transfer product may be produced using resting microorganisms.

A method which uses resting microorganisms simply employs a culture solution as is. Another method comprises isolating cells by centrifugation, or an equivalent technique, resuspending the cells in phosphate buffer or equivalent, further adding lactose or a galactose donor such as o-nitrophenyl-β-D-galactopyranoside, or the like and a galactose receptor such as sugar, sugar alcohol, a nucleoside, alcohol or derivative thereof, to the suspension and then reacting these ingredients. The microorganisms may be viable cells or the cells may have been subjected to treatment with acetone or may have been subjected to freeze drying. Furthermore, the microorganism may also have been immobilized on a carrier or it may have been used in a bioreactor utilizing an ultrafiltration membrane.

In the reaction in which the galactose transfer product is formed from lactose or a galactose donor such as o-nitrophenyl-β-D-galac-topyranoside, or the like and a galactose receptor such as sugar, a sugar alcohol, a nucleoside, an alcohol or derivatives thereof, the amounts of lactose or the-galactose donor and the galactose receptor employed are not particularly limited, but the amount is in a range of 0.5 to 70 wt. %, preferably in a range of 1 to 30 wt. %, when calculated as lactose. When o-nitrophenyl-β-D-galactopyranoside, the amount ranges from 0.2 to 10 wt. %, preferably 0.5 to 2 wt. %. When calculated as the sugar, sugar alcohol, nucleoside, alcohol or derivatives thereof, the amount ranges from 0.1 to 50 wt. %, preferably 1.0 to 30 wt. %. The reaction is carried out at a temperature of generally 20° to 70° C., preferably 25° to 65° C. at a pH range of from 2 to 10, preferably 3 to 7, for 2 hours to 10 days.

After the reaction is completed, if necessary, the cells are removed, and the galactose transfer product is isolated from the reaction solution by a technique using a exchange resin, by gel filtration, by adsorption with activated charchoal, by chromatography or the like. The galactose transfer product can then be purified.

Having generally described this invention, a further understanding can be obtained by reference to certain specific examples which are provided herein for purposes of illustration only and are not intended to be limiting unless otherwise specified.

Lactose and galactose transfer product were quantitatively analyzed for by determination of the peak area of a high performance liquid chromatograms (pump: Model 655 manufactured by Hitachi Ltd., detector: SE-51 manufactured by Showa Denko Co., Ltd.; column: Shodex-S801; solvent:water).

EXAMPLE 1

Into a flask of a 500 ml volume was charged 50 ml of a medium (pH 7.0) containing 1.0 g/dl of lactose, 1.0 g/dl of glycerol, 1.0 g/dl of yeast extract, 1.0 g/dl of polypeptone, 0.5 g/dl of $(NH_4)_2SO_4$, 0.3 g/dl of $K_2HPO_4$, 0.1 g/dl of $KH_2PO_4$ and 0.05 g/dl of $MgSO_4 \cdot 7H_2O$. The medium was then sterilized at 115° C. for 15 minutes. A plurality of such media were each inoculated with a platinum loop of one of the microorganism strains of *Rhodotorula minuta* IFO 879, *Sterigmatomyces elviae* AJ 14199 (FERM BP-2586, FERM P-10001), *Cryptococcus laurentii* IFO 609, *Geotrichum amycelicum* AJ 14196 (FERM P-10071), *Apiotrichum humicola* ATCC 14438 and *Sirobasidium magnum* CBS 6803, each of which had been cultured in a malt extract agar medium at 25° C. for 2 days, and *Corynebacterium michiganense* ATCC 492, *Bacillus megaterium* AJ 1272 (FERM P-3747), *Flavobacterium aurantianum* AJ 2462 (FERM P-10069) and *Rhizobium meliloti* AJ 2823 (FERM P-8197), which had been cultured in a bouillon agar medium at 30° C. for 24 hours. The inoculated media were then cultured with shaking at 30° C. for 2 days in the cases of cultures of IFO 879, AJ 14199 (FERM BP-2586, FERM P-10001), IFO 609, AJ 14196 (FERM P-10071), ATCC 14438 and CBS 6803, and for 24 hours in the cases of cultures of ATCC 492, AJ 1272 (FERM P-3747), AJ 2462 (FERM P-10069) and AJ 2823 (FERM P-8197).

The bacterial cells were resuspended in 50 ml of substrate solution (in 50 mM phosphate buffer, pH 7.0) supplemented with 2.5 g of lactose and 5 g each of the sugars shown in Table 1. Reaction was allowed to proceed at 50° C. for 24 hours. The amounts of galactose transfer product in each of the reaction solutions are shown in Table 1.

TABLE 1

Amount of Galactose Transfer Product of Each Sugar (total $(GAL)_n - R$) (g/dl)

| | Lactulose | Raffinose | Melibiose | Galactose | Ribose | Arabinose | Xylose | Rhamnose |
|---|---|---|---|---|---|---|---|---|
| *Rhodotorula minuta* IFO 879 | 1.7 | 1.2 | 1.2 | 1.4 | 1.5 | 1.2 | 1.0 | 0.8 |
| *Sterigmatomyces elviae* AJ 14199 (FERM BP-2586) (FERM P-10001) | 1.8 | 0 | 1.3 | 1.4 | 1.6 | 1.2 | 1.1 | 0.8 |
| *Cryptococcus laurentii* IFO 609 | 1.2 | 0 | 0 | 0.3 | 0.4 | 0 | 0.3 | 0 |
| *Geotrichum amycelicum* AJ 14196 (FERM P-10071) | 1.4 | 0.4 | 0.9 | 0.2 | 0.2 | 0.2 | 0 | 0 |
| *Apiotrichum humicola* ATCC 14438 | 1.1 | 0.3 | 0.7 | 0.2 | 0.2 | 0 | 0 | 0 |
| *Sirobasidium magnum* CBS 6803 | 1.6 | 0.5 | 1.3 | 1.4 | 1.2 | 1.1 | 1.0 | 0.6 |
| *Corynebacterium michiganensis* ATCC 492 | 1.0 | 0.6 | 0.8 | 0.2 | 0.3 | 0.6 | 0.8 | 0 |
| *Bacillus megaterium* AJ 1272 (FERM P-3747) | 0.8 | 0.1 | 0.3 | 0.2 | 0.3 | 0 | 0 | 0 |
| *Flavobaterium aurantianum* AJ 2462 (FERM P-10069) | 0.8 | 0.4 | 0.4 | 0.2 | 0.3 | 0.5 | 0.6 | 0.1 |
| *Rhizobium meliloti* AJ 2823 (FERM P-8197) | 0.8 | 0.5 | 0.8 | 0.2 | 0.2 | 0.7 | 0.7 | 0.2 |

| | 2-Deoxyglucose | Sorbose | N-acetylglucosamine | Fructose | α-Methylglucoside | α-Methylmannoside |
|---|---|---|---|---|---|---|
| *Rhodotorula minuta* IFO 879 | 0.7 | 0.9 | 0.4 | 0.3 | 0.5 | 0.4 |
| *Sterigmatomyces elviae* AJ 14199 (FERM BP-2586) (FERM P-10001) | 0.8 | 1.0 | 0.5 | 0.2 | 0.6 | 0.5 |
| *Cryptococcus laurentii* IFO 609 | 0.2 | 0.2 | 0 | 0.1 | 0 | 0 |
| *Geotrichum* | 0.2 | 0.3 | 0 | 0.1 | 0 | 0 |

TABLE 1-continued

| Amount of Galactose Transfer Product of Each Sugar (total (GAL)n − R) (g/dl) | | | | | | |
|---|---|---|---|---|---|---|
| amycelicum AJ 14196 (FERM P-10071) | | | | | | |
| Apiotrichum humicola ATCC 14438 | 0.2 | 0.3 | 0 | 0 | 0 | 0 |
| Sirobasidium magnum CBS 6803 | 0.5 | 0.8 | 0.3 | 0.3 | 0.3 | 0.3 |
| Corynebacterium michiganensis ATCC 942 | 0.3 | 0.3 | 0 | 0.1 | 0 | 0 |
| Bacillus megaterium AJ 1272 (FERM P-3747) | 0.2 | 0.2 | 0 | 0 | 0 | 0 |
| Flavobaterium aurantianum AJ 2462 (FERM P-10069) | 0.3 | 0.3 | 0 | 0 | 0 | 0 |
| Rhizobium meliloti AJ 2823 (FERM P-8197) | 0.4 | 0.3 | 0 | 0 | 0 | 0 |

EXAMPLE 2

The cells were prepared in a manner similar to the procedure of Example 1. The prepared cells were resuspended in 50 ml of substrate solution (in 50 mM phosphate buffer, pH 7.0) supplemented with 2.5 g of lactose and 5 g each of the sugar alcohols and alcohols shown in Table 2. Reaction was allowed to proceed at 50° C. for 24 hours. The amounts of galactose transfer product in the reaction solutions are shown in Table 2.

TABLE 2

| Amount of Galactose Transfer Product to Each Sugar Alcohol and Alcohol (total (GAL)n − R) (g/dl) | | | | | |
|---|---|---|---|---|---|
| | Inositol | Sorbitol | Mannitol | Xylitol | Glycerol |
| Rhodotorula minuta IFO 879 | 2.2 | 2.1 | 2.3 | 1.2 | 0.9 |
| Sterigmatocymes elviae AJ 14199 (FERM BP-2586) (FERM P-10001) | 2.4 | 2.2 | 2.4 | 1.3 | 0.8 |
| Cryptococcus laurentii IFO 609 | 0.6 | 0.5 | 0.5 | 1.0 | 0.6 |
| Geotrichum amycelicum AJ 14196 (FERM P-10071) | 0.4 | 0.4 | 0.5 | 0.4 | 0.2 |
| Apiotrichum humicola ATCC 14438 | 0 | 0.1 | 0.1 | 0.3 | 0.2 |
| Sirobasidium magnum CBS 6803 | 2.0 | 2.0 | 2.1 | 1.0 | 0.7 |
| Corynebacterium michiganensis ATCC 492 | 0.2 | 0.3 | 0.2 | 0.3 | 0.4 |
| Bacillus megaterium AJ 1272 (FERM P-3747) | 0 | 0.1 | 0.1 | 0.2 | 0.2 |
| Flavobaterium aurantianum AJ 2462 (FERM P-10069) | 0.2 | 0.2 | 0.2 | 0.3 | 0.4 |
| Rhizobium meliloti AJ 2823 (FERM P-8197) | 0 | 0.1 | 0.2 | 0.3 | 0.5 |

EXAMPLE 3

The cells were prepared in a manner similar to the procedure of Example 1. The prepared cells were resuspended in 10 ml of substrate solution (in 50 mM phosphate buffer, pH 7.0) supplemented with 0.5 g of lactose and 1.0 g each of the nucleosides shown in Table 3. Reaction was allowed to proceed at 50° C. for 24 hours. The amounts of galactose transfer product in the reaction solutions are shown in Table 3.

TABLE 3

| Amount of Galactose Transfer Product to Each Nucleoside (total (GAL)n − R) (g/dl) | | | | | | |
|---|---|---|---|---|---|---|
| | Adenosine | Guanosine | Inosine | Cytidine | Uridine | 2'-Deoxyadenosine |
| Rhodotorula minuta IFO 879 | 1.8 | 0.3 | 2.6 | 2.6 | 2.6 | 2.4 |
| Sterigmatomyces elviae AJ 14199 (FERM BP-2586) (FERM P-10001) | 1.9 | 0.2 | 2.7 | 2.6 | 2.6 | 2.3 |
| Cryptococcus laurentii IFO 609 | 1.3 | 0 | 1.5 | 1.6 | 1.5 | 1.4 |
| Geotrichum amycelicum AJ 14196 (FERM P-10071) | 1.2 | 0.1 | 0.6 | 1.0 | 0.9 | 0.6 |
| Apiotrichum humicola ATCC 14438 | 0.4 | 0.2 | 0.5 | 0.3 | 0.3 | 0.3 |
| Sirobasidium magnum CBS 6803 | 1.7 | 0.1 | 2.4 | 2.5 | 2.4 | 2.2 |
| Corynebacterium michiganensis ATCC 492 | 1.3 | 0.1 | 1.0 | 1.3 | 1.1 | 0.4 |
| Bacillus megaterium AJ 1272 (FERM P-3747) | 0.6 | 0.1 | 0.5 | 0.2 | 0.3 | 0.2 |
| Flavobaterium aurantianum AJ 2462 (FERM P-10069) | 1.2 | 0.2 | 0.8 | 1.2 | 1.0 | 0.6 |
| Rhizobium meliloti AJ 2823 (FERM P-8197) | 1.1 | 0.2 | 0.9 | 1.1 | 0.8 | 0.5 |

EXAMPLE 4

The cells were prepared in a manner similar to the procedure of Example 1. The prepared cells were resuspended in 10 ml of substrate solution (in 50 mM phosphate buffer, pH 7.0) supplemented with 0.15 g of o-nitrophenyl-β-D-galactopyranoside and 1.0 g each of the nucleosides shown in Table 4. Reaction was allowed to proceed at 50° C. for 20 hours. The amounts of galactose transfer product in the reaction solutions are shown in Table 4.

TABLE 4

Amount of Galactose Transfer Product to Each Nucleoside (total (GAL)n — R) (g/dl)

| | Adenosine | Guanosine | Inosine | Cytidine | Uridine | 2'-Deoxy-adenosine |
|---|---|---|---|---|---|---|
| Rhodotorula minuta IFO 879 | 0.7 | 0.2 | 1.3 | 1.3 | 1.3 | 1.3 |
| Sterigmatomyces elviae AJ 14199 (FERM BP-2586) (FERM P-1001) | 0.7 | 0.2 | 1.4 | 1.4 | 1.4 | 1.3 |
| Cryptococcus laurentii IFO 609 | 0.4 | 0.1 | 0.8 | 0.9 | 0.8 | 0.2 |
| Geotrichum amycelicum AJ 14196 (FERM P-10071) | 0.4 | 0.1 | 0.3 | 0.5 | 0.4 | 0.1 |
| Apiotrichum humicola ATCC 14438 | 0.1 | 0.1 | 0.2 | 0.1 | 0.1 | 0.2 |
| Sirobasidium magnum CBS 6803 | 0.6 | 0.2 | 1.2 | 1.3 | 1.3 | 1.3 |
| Corynebacterium michiganensis ATCC 492 | 0.6 | 0.1 | 0.6 | 0.5 | 0.6 | 0.2 |
| Bacillus megaterium AJ 1272 (FERM P-3747) | 0.3 | 0.1 | 0.2 | 0.1 | 0.1 | 0.1 |
| Flavobaterium aurantianum AJ 2462 (FERM P-10069) | 0.5 | 0.2 | 0.4 | 0.6 | 0.5 | 0.3 |
| Rhizobium meliloti AJ 2823 (FERM P-8197) | 0.5 | 0.1 | 0.5 | 0.6 | 0.4 | 0.3 |

EXAMPLE 5

The cells of Rhodotorula minuta IFO 879 were prepared in a manner similar to the procedure of Example 1. The prepared cells were resuspended in 50 ml of substrate solution (in 50 mM phosphate buffer, pH 7.0) supplemented with 2.5 g of lactose and 5 g inosine. Reaction was allowed to proceed at 50° C. for 48 hours. The amounts of galactose transfer product in the reaction solution are shown in Table 5.

TABLE 5

Amount of Galactose Transfer Products Based on Inosine (g/dl)

| Number of Galactose Residue: 1 | Number of Galactose Residue: 2 | Number of Galactose Residue: 3 or more |
|---|---|---|
| 1.4 | 0.8 | 0.4 |

EXAMPLE 6

Into a flask of a 500 ml volume was charged 50 ml of a medium (pH 7.0) containing 10.0 g/dl of lactose, 2.0 g/dl of glycerol, 0.05 g/dl of yeast extract, 0.5 g/dl of $(NH_4)_2SO_4$, 0.3 g/dl of $K_2HPO_4$, 0.1 g/dl of $KH_2PO_4$ and 0.005 g/dl of $MgSO_4 \cdot 7H_2O$. The medium was then sterilized at 115° C. for 15 minutes.

Each of several samples of the medium was inoculated with a platinum loop of Rhodotorula minuta IFO 879, Sterigmatomyces elviae FERM P-10001 or Sirobasidium magnum CBS 6803, which had been cultured in a malt extract agar medium at 25° C. for 2 days. Each inoculated medium was then cultured with shaking at 30° C. for 4 days. The amount of the galacto-oligosaccharide product produced in each of supernatants in the culture solutions is shown in Table 6.

TABLE 6

| | Residual Lactose (g/dl) | Produced Galacto-oligosaccharide | |
|---|---|---|---|
| | | Trisaccharide (g/dl) | Tetrasaccharide or more (g/dl) |
| Rhodotorula minuta IFO 879 | 0.8 | 4.2 | 2.6 |
| Sterigmatomyces elviae FERM BP-2586 FERM P-10001 | 2.1 | 6.7 | 0 |
| Sirobasidium magnum CBS 6803 | 1.8 | 5.2 | 1.9 |

EXAMPLE 7

Into a flask of a 500 ml volume was charged 50 ml of a medium (pH 7.0) containing 1.0 g/dl of lactose, 2.0 g/dl of glycerol, 1.0 g/dl of yeast extract, 1.0 g/dl of polypeptone, 0.5 g/dl of $(NH_4)SO_4$, 0.3 g/dl of $K_2HPO_4$, 0.1 g/dl of $KH_2PO_4$ and 0.05 g/dl of $MgSO_4 \cdot 7H_2O$. The thus prepared medium was sterilized at 115° C. for 15 minutes.

Each of several samples of the medium was then inoculated with a platinum loop of Rhodotorula minuta IFO 879, Sterigmatomyces elviae FERM P-10001 or Sirobasidium magnum CBS 6803, which had been cultured in a malt extract agar medium for 2 days. Each inoculated medium was then cultured with shaking at 30° C. for 4 days. After completion of the culturing, the bacterial cells were collected from each medium by centrifugation and were then washed once with the same amount of physiological saline as the culture solution from which the cells had been collected.

The cells were resuspended in 50 ml of 22 g/dl of lactose solution (in 50 mM phosphate buffer, pH 7.0). Reaction was allowed to proceed at 50° C. for 2 days. The sugar composition of each reaction solution is shown in Table 7.

TABLE 7

| | Residual Lactose (g/dl) | Produced Galacto-oligosaccharide | |
|---|---|---|---|
| | | Trisaccharide (g/dl) | Tetrasaccharide or more (g/dl) |
| Rhodotorula minuta IFO 879 | 9.6 | 8.4 | 1.7 |
| Sterigmatomyces | 10.5 | 9.3 | 0 |

TABLE 7-continued

| | Residual Lactose (g/dl) | Produced Galacto-oligosaccharide | |
|---|---|---|---|
| | | Trisaccharide (g/dl) | Tetrasaccharide or more (g/dl) |
| elviae FERM BP-2586 FERM P-10001 | | | |
| Sirobasidium magnum CBS 6803 | 11.2 | 8.0 | 0.6 |

EXAMPLE 8

Into a fermenter of a 5 liter volume was charged 2 l of a medium of pH 7.0 containing 1.0 g/dl of lactose, 2.0 g/dl of glycerol, 1.0 g/dl of yeast extract, 1.0 g/dl of polypeptone, 0.5 g/dl of $(NH_4)_2SO_4$, 0.3 g/dl of $K_2HPO_4$, 0.1 g/dl of $KH_2PO_4$ and 0.05 g/dl of $MgSO_4 \cdot 7H_2O$. Media prepared in this manner were inoculated with a sample of *Rhodotorula minuta* IFO 879, *Sterigmatomyces elviae* FERM P-10001 or *Sirobasidium magnum* CBS 6803. Each inoculated medium was then aerobically cultured at 30° C. for 36 hours with agitation at 500 rpm in an aerial amount of ½ vvm. Each culture solution was centrifuged to isolate the bacterial cells, which were used as an enzyme source. Then the following steps were performed.

Step (1): The resulting cells were suspended in 2 l of 36 g/dl of lactose solution (in 50 mM phosphate buffer, pH 6.0). Reaction was allowed to proceed at 30° C. while performing aerial agitation.

Step (2): After reaction for 3 days, the reaction solution was subjected to recycling filtration through an ultrafiltering polysulfone membrane (manufactured by Amicon Inc.) until the outer solution became 1000 ml. Then, the amount of the inner solution, the concentration of lactose and pH were adjusted to 2 l, 36 g/dl and 6.0, respectively. The operation of step (2) was repeated 4 times. The concentration of galacto-oligosaccharide product in each outer solution obtained by this operation is shown in Table 8. Ultrafiltration was carried out under a mean filtering pressure of 1 kg/cm² at a temperature of 30° C.

In each embodiment of the example, the mean filtering pressure and temperature of ultrafiltration were the same.

TABLE 8

| | Concentration of Galacto-oligosaccharide in Outer Solution (g/dl) | | | | |
|---|---|---|---|---|---|
| Enzyme Source: | Number of Operation | First | Second | Third | Fourth |
| *Rhodotorula minuta* IFO 879 | | 21.6 | 22.6 | 21.2 | 21.3 |
| *Sterigmatomyces elvaie* FERM BP-2586 FERM P-10001 | | 21.4 | 21.2 | 20.8 | 20.6 |
| *Sirobasidium magnum* CBS 6803 | | 19.5 | 19.3 | 19.8 | 18.9 |

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United State is:

1. A method for producing a galactose transfer product, which comprises:
    allowing a microorganism strain of the genus Sterigmatomyces, Sirobasidium or Rhodotorula, which is capable of producing a galactose transfer product of the formula $(Gal)_n$—R, wherein Gal represents a galactose residue, n represents an integer of 1 to 4 and R represents sugar as a galactose receptor to act on a combination of lactose and galactose receptor at 20° to 70° C. at a pH of 2 to 10; and
    collecting the galactose transfer product produced.
2. The method of claim 1 wherein the amount of galactose receptor ranges from 0.1 to 50 wt. %.
3. The method of claim 1, wherein the amount of lactose ranges from 0.5 to 70 wt. %.
4. The method of claim 1, wherein the microorganism strain acts on the lactose and galactose receptor for 2 hours to 10 days.
5. The method of claim 1, wherein said microorganism strain is of the species *Sterigmatomyces elviae.*
6. The method of claim 1, wherein said microorganism strain is of the species *Sirobasidium magnum.*
7. The method of claim 1, wherein said microorganism strain is of the species *Rhodotorula minuta.*
8. The method of claim 1, wherein said microorganism strain is of the species *Rhodotorula maraina.*
9. The method of claim 1, wherein said microorganism strain is *Sterigmatomyces elviae* FERM-BP-2586, FERM-P-10001.
10. The method of claim 1, wherein said galactose transfer product has the formula (Gal)-Lac.
11. The method of claim 1, wherein said temperature ranges from 25° to 65° C. and said pH ranges from 3 to 7.

* * * * *

UNITED STATES PATENT AND TRADEMARK OFFICE
CERTIFICATE OF CORRECTION

PATENT NO. : 5,149,640
DATED : September 22, 1992
INVENTOR(S) : Norimasa Onishi, et al It is certified that error appears in the above-indentified patent and that said Letters Patent is hereby corrected as shown below:

On the title page, Item [75] Inventor: delete "Oonishi" and insert --Onishi-- and also change Item [19]:

Col. 1 line 33, delete "no." and insert --No.--
Col. 2 line 63, delete "galac-topyranoside" and insert --galactopyranoside--
Col. 4 line 25, delete "bacterial" and after "cells" insert --collected from each medium by centrifugation--
Col. 8 line 53, delete "bacterial"
Col. 9 line 31, delete "bacterial"
Col. 10 line 2 Claim 4, after "and" insert --a--

Signed and Sealed this

Second Day of November, 1993

Attest:

BRUCE LEHMAN

*Attesting Officer*  Commissioner of Patents and Trademarks